United States Patent [19]

Peet et al.

[11] Patent Number: 4,761,474

[45] Date of Patent: Aug. 2, 1988

[54] 3-(1H-TETRAZOL-5-YL)THIENO[2,3-D]PYRIMIDIN-4(3H)-ONES

[75] Inventors: Norton P. Peet; Shyam Sunder, both of Indianapolis, Ind.; Anna P. Vinogradoff, Concord, Calif.

[73] Assignee: Merrell Dow Pharmaceuticals Inc., Cincinnati, Ohio

[21] Appl. No.: 833,871

[22] Filed: Feb. 25, 1986

[51] Int. Cl.$^4$ ............................................. C07D 495/04
[52] U.S. Cl. .................... 544/250; 544/278; 548/251; 549/57; 549/59; 549/68
[58] Field of Search ................................ 544/278, 250

[56] References Cited

U.S. PATENT DOCUMENTS

| | | | |
|---|---|---|---|
| 4,054,656 | 10/1977 | Temple, Jr. | 424/251 |
| 4,159,377 | 6/1979 | Temple, Jr. | 544/278 |
| 4,419,357 | 12/1983 | Peet et al. | 544/284 |
| 4,644,065 | 2/1987 | Vinogradoff | 544/250 |

FOREIGN PATENT DOCUMENTS

| | | |
|---|---|---|
| 2401163 | 3/1979 | France . |
| 1583679 | 1/1981 | United Kingdom . |
| 2113220 | 8/1983 | United Kingdom ................ 544/250 |

OTHER PUBLICATIONS

Bohm et al., *Pharmazie*, 38(2), 135, 136 (1983).
Conner et al., *J. Med. Chem.*, 27, 528 (1984).
Haubold et al., *Pharmazie*, 38(4), 269 (1983).
Ried et al., *Ann. Chem.*, 713, 143 (1968).
Schellhase et al., *Pharmazie*, 39(1), 19 (1984).
Shishoo et al., *Indian J. Chem.*, 21B, 666 (1982).
Shishoo et al., *J. Het. Chem.*, 21(2), 375 (1984).
Temple et al., *J. Med. Chem.*, 22, 505 (1979).
Tinney et al., *J. Med. Chem.*, 24, 878 (1981).

*Primary Examiner*—Robert Gerstl
*Assistant Examiner*—E. Bernhardt
*Attorney, Agent, or Firm*—John J. Kolano

[57] ABSTRACT

3-(1H-Tetrazol-5-yl)thieno[2,3-d]pyrimidin-4(3H)-ones useful as antiallergic agents are described herein. The compounds are prepared by cyclization of an appropriate substituted amidine using an alkali metal base. The reaction is carried out in an appropriate inert solvent.

5 Claims, No Drawings

3-(1H-TETRAZOL-5-YL)THIENO[2,3-D]PYRIMIDIN-4(3H)-ONES

The present invention relates to a group of thieno[2,3-d]pyrimidin-4(3H)-ones substituted with a tetrazole group. More particularly, the present invention relates to a group of compounds having the following general formula

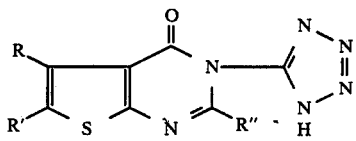

wherein R is hydrogen or lower alkyl containing 1 to 4 carbon atoms; R' is hydrogen, lower alkyl containing 1 to 4 carbon atoms or phenyl; or R and R' combined are trimethylene or tetramethylene; R" is hydrogen, methyl or ethyl; and the pharmaceutically acceptable salts thereof.

Examples of the lower alkyl groups referred to above are methyl, ethyl, propyl and butyl. Hydrogen is preferred for R". Equivalent for the purposes of this invention are the pharmaceutically acceptable salts and also the hydrates of the compounds and their salts. The term "pharmaceutically acceptable salt" as used herein is intended to include non-toxic cationic salts such as the alkali metal salts, e g., sodium and potassium; alkaline earth metal salts such as calcium, magnesium or barium; salts with ammonia; and salts with organic bases, e.g., amines such as triethylamine, n-propylamine and tri-n-butylamine. The alkali metal salts and, particularly the sodium salt, are preferred.

The compounds of the present invention are prepared by the cyclization of an amidine having the following structural formula

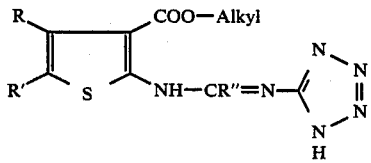

wherein R, R' and R" are defined as above and alkyl is methyl or ethyl. The reaction is carried out in the presence of a base such as aqueous sodium hydroxide in a solvent such as 2-propanol. Heating may be used to complete the reaction. Since the reaction is carried out under alkaline conditions, the product is obtained as the salt of the tetrazole. Specifically, the sodium salt is obtained when sodium hydroxide is used in the cyclization. If the free tetrazole itself is desired, an aqueous solution of the sodium or other salt is acidified and the desired product is isolated according to standard procedures. The resulting tetrazole free acid can be converted to pharmaceutically acceptable salts by reacting it with a substantially equimolar amount of the appropriate base in an aqueous solution or in a suitable organic solvent, such as methanol or ethanol. The salts are recovered by standard methods such as filtration if they are insoluble in the original medium, or, if they are soluble in that medium, the salt is precipitated by evaporation of the solvent or by addition of a non-solvent for the salt.

The amidine starting material used above is obtained by the reaction of an alkyl 2-aminothiophene-3-carboxylate with an imidate of the formula

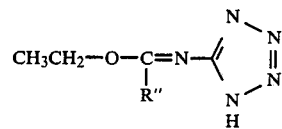

The reaction is carried out by adding the amino ester to the imidate as obtained in situ in an inert solvent such as dimethylformamide. Depending on the specific reactants involved, the indicated process may provide the desired amidine or a mixture of the desired amidine with a symmetrical amidine obtained as a byproduct of the process. If such a mixture is obtained and the compounds cannot be separated, then the mixture itself can be used in the subsequent cyclization process and removal of any undesired materials can be accomplished at the final-product stage.

The compounds of the present invention possess antiallergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermatitis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maize-starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or another suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human asthmatic patients in single oral doses of approximately 1–1000 mg of active ingredient and multiple oral doses totaling up to about 4000 mg/day of active ingredient. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The antiallergic activity of the present compounds is demonstrated by the IgE mediated rat Passive Cutaneous Anaphylaxis (PCA) test. This test is generally accepted as one of the best animal models for the qualitative determination of antiallergic activity. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.
2. Animals—Adult male Sprague-Dawley or female Wistar Kyoto rats were used as antisera recipients in the test. The animals were allowed to acclimate for 5–14 days with food and water ad lib.
3. Sensitization—Recipient rats were passively sensitized by the intradermal injection of 100 microliters of two dilutions of antiserum (one injection on each side of the back). Sensitization occurred 48–72 hours prior to antigen challenge.
4. Administration of Test Compound—Four to six animals were used for each test compound/dilution. Compounds were homogenized in an appropriate carrier solution, and administered i.p. at 60 mg/kg 5 minutes prior to challenge or p.o. at 100 mg/kg 5 to 360 minutes prior to challenge.
5. Antigen Challenge and Reaction Evaluation—Ovalbumin (0.1–1.0 mg in a 0.5% solution of Evan's Blue Dye) in saline were given to each rat by i.v. administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active both i.p. and orally.

As indicated earlier, those compounds wherein R″ is hydrogen are preferred. In addition to activity in the PCA test as described above, the compounds wherein R″ is hydrogen also inhibit the release of histamine in the rat Passive Peritoneal Anaphylaxis (PPA) test. This method can be described briefly as follows:

PPA TEST METHOD

1. Antisera—Reaginic antibody to ovalbumin for this test was prepared in adult male $B_6D_2F_1$ mice.
2. Animals—Adult male Sprague Dawley or female Wistar Kyoto rats were used as antibody recipients. The animals were allowed to acclimate for 5–14 days with food and water ad lib.
3. Sensitization—Recipient rats were sensitized i.p. with 2 ml of an appropriate saline dilution of the mouse anti-ovalbumin antiserum determined from prior experiments. Sensitization took place 2 hours prior to antigen challenge.
4. Administration of Test Compound—Five to ten animals were used for each test compound/dilution. Compounds were homogenized in saline with an equivalent of sodium bicarbonate to effect solubilization, if appropriate, and administered i.p. at 60 μg, 30 seconds prior to antigen challenge or p.o. 5 to 60 minutes prior to antigen challenge.
5. Antigen Challenge and Assay Evaluation—Two mg of ovalbumin in 5 ml of modified Tyrode's Solution was administered by i.p. injection and the animals were sacrificed 5 minutes later. Peritoneal shock fluids were collected and classified by centrifugation. Protein was removed from the samples by perchloric acid precipitation and subsequent centrifugation. The samples were then analyzed for histamine content by an automated fluorometric assay. Histamine levels of peritoneal shock fluids from treatment animals were then compared to those of shock fluids from control animals Drug effect was expressed as percent inhibition of histamine release.

As indicated earlier, the compounds of the present invention are active as anti-allergic agents. However, certain compounds are considered to be particularly useful because they have a prolonged duration of effect. Thus, those compounds wherein R″ is hydrogen are generally preferred and, within that group, certain compounds are particularly preferred because of their prolonged effect. Specifically useful in this regard are the compounds wherein R′ is propyl; R and R′ are both methyl; or R and R′ are combined as tetramethylene.

The following examples are presented to illustrate the present invention but they should not be construed as limiting it in any any.

EXAMPLE 1

To a mixture of 56.6 g of ethyl cyanoacetate, 16.0 g of sulfur, 40 ml of triethylamine and 80 ml of dimethylformamide there was added 43.1 g of n-valeraldehyde at such a rate that the temperature was maintained below 50° C. After 1 hour of stirring, the mixture was partitioned between water and dichloromethane. The organic layer was dried over sodium sulfate and concentrated and the oil obtained was purified by Kugelrohr distillation (140°–160° C.) to give ethyl 2-amino-5-propylthiophene-3-carboxylate as a yellow oil.

EXAMPLE 2

A mixture of 56.6 g of ethyl cyanoacetate, 43.1 g of 3-pentanone, 16.0 g of sulfur, 50 ml of morpholine and 150 ml of ethanol was heated at 50° C. for 3 hours. A small amount of yellow solid remained undissolved. After stirring for 3 days, the mixture was filtered and the filtrate was concentrated and partitioned between dichloromethane and water. The organic layer was separated and dried over sodium sulfate and then concentrated, and the resulting oil was purified by Kugelrohr distillation (160° C.) to give a yellow oil. Redistillation of this material gave ethyl 2-amino-4-ethyl-5- methylthiophene-3-carboxylate which solidified on standing to a yellow solid which melted at about 40°–41° C.

EXAMPLE 3

A mixture of 20.0 g of 5-aminotetrazole and 39 ml of triethoxymethane in 75 ml of dimethylformamide was heated at 100° C. for 2.5 hours with stirring. A solution of 44.5 g of ethyl 2-amino-5-methylthiophene-3-carboxylate in 30 ml of dimethylformamide was added and the mixture was stirred for 5 minutes. Heating was then discontinued and the mixture was allowed to cool to ambient temperature and it was filtered. The solid collected was washed with dimethylformamide and then with tetrachloromethane and dried in a vacuum oven at 40° C. to give crude N-(1H-tetrazol-5-yl)-N'-(5-methyl-3-carbethoxythiophen-2-yl)formamidine. Recrystallization of a sample from methanol gave a solid melting at about 218° C. with decomposition.

EXAMPLE 4

A mixture of 48 ml of triethoxymethane, 12.0 g of 5aminotetrazole, 1 ml of 95% formic acid and 200 ml of tetrachloromethane was heated in an apparatus equipped for distillation. This mixture was heated, distillate was collected, and tetrachloromethane was added to the reaction vessel to replace distilled material, as necessary, until proton NMR of aliquots filtered from the heterogeneous mixture showed signals for imidate and no 5-aminotetrazole. Approximately 6 hours was necessary. Then, 29.5 g of ethyl 2-amino-4,5-dimethylthiophene-3-carboxylate was added to the reaction mixture in one portion as a solid and the mixture was heated for an additional 30 minutes. A dense precipitate formed and the mixture was cooled to room temperature. The solid was collected by filtration, washed well with methanol and dried in a vacuum oven at 40° C. to give crude N-(1H-tetrazol-5-yl)-N'-(3-carbethoxy-4,5-dimethylthiophen-2-yl)formamidine as a fine pale yellow powder. Recrystallization of a sample from aqueous methanol gave a solid melting at about 182°–183° C.

EXAMPLE 5

The procedure of Example 4 was repeated using ethyl 2-amino-4,5-tetramethylenethiophene-3-carboxylate, added in 20 portions, in place of the ethyl 2-amino-4,5-dimethylthiophene-3-carboxylate. The crude product obtained was N-(1H-tetrazol-5-yl)-N'-(3-carbethoxy-4,5-tetramethylenethiophen-2-yl)formamidine as a pale yellow powder. Recrystallization of a sample from aqueous 2-propanol gave a purified solid melting at about 201°–202° C. with decomposition.

EXAMPLE 6

A mixture of 40 ml of triethoxymethane, 10.0 g of 5-aminotetrazole, 1 ml of 95% formic acid and 200 ml of tetrachloromethane was heated in an apparatus equipped with a distilling condenser. Distillate was collected and tetrachloromethane in the reaction vessel was replaced, as necessary, until proton NMR of aliquots filtered from the heterogeneous mixture showed signals for imidate and no 5-aminotetrazole. About 6 hours was necessary. A solution of 55.7 g of ethyl 2-amino-5-propylthiophene-3-carboxylate in 100 ml of tetrachloromethane was added to the reaction mixture which was then stirred for 20 minutes before it was allowed to cool to room temperature. The solid which formed was separated by filtration, washed well with tetrachloromethane and dried in a vacuum oven to give crude N-(1H-tetrazol-5-yl)-N'-(5-propyl-3-carbethoxythiophen-2-yl)formamidine as a pale yellow powder. A slurry of 6 g of this crude formamidine in 30 ml of methanol was stirred at room temperature as 3.9 ml of 5 N sodium hydroxide was added dropwise. The mixture was then heated at 65° C. for 13 hours and cooled to room temperature. The solvent was evaporated in vacuo and the residual material was taken up in hot aqueous 2-propanol for recrystallization. The solid which formed was collected by filtration, washed with cold aqueous 2-propanol and dried in a vacuum oven to give 3-(1H-tetrazol-5-yl)-6-propylthieno[2,3-d]pyrimidin-4(3H)-one, sodium salt hemihydrate as hygroscopic off-white needles melting at greater than 275° C. Acidification of an aqueous solution of this product gives 3-(1H-tetrazol-5-yl)-6-propylthieno[2,3-d]pyrimidin-4(3H)-one. This compound has the following structural formula:

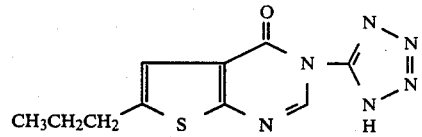

EXAMPLE 7

A mixture of 20 ml of triethoxymethane and 6.55 g of 5-aminotetrazole was converted to the imidate as described in Example 6. Then, a slurry of 20.1 g of ethyl 2-amino-5-phenylthiophene-3-carboxylate in 40 ml of tetrachloromethane was added to the reaction mixture which was stirred for 30 minutes as a dense slurry formed. The mixture was cooled to room temperature, the solid was collected by filtration, washed well with tetrachloromethane and dried in a vacuum oven to give crude N-(1H-tetrazol-5-yl)-N'-(5-phenyl-3-carbethoxythiophen-2-yl)formamidine as a yellow powder. A slurry of 7 g of this crude formamidine in 70 ml of methanol was stirred at room temperature and 4.2 ml of 5 N aqueous sodium hydroxide was added dropwise. The solution became homogeneous and it was heated at reflux for 44 hours during which time it became heterogeneous. The mixture was cooled to room temperature, the solid was separated by filtration, washed well with methanol and dried in a vacuum oven to give crude 3-(1H-tetrazol-5-yl)-6-phenylthieno[2,3-d]pyrimidin-4(3H)-one, sodium salt. Recrystallization of the crude product twice from hot aqueous 2-propanol gave purified product as a 0.75 hydrate melting at greater than 275° C.

EXAMPLE 8

A mixture of 33 ml of triethoxymethane, 17 g of 5-aminotetrazole and 75 ml of dimethylformamide was heated at 105° C. for 2 hours. A solution of 20 g of ethyl 2-amino-4-ethyl-5-methylthiophene-3-carboxylate in 40 ml of dimethylformamide was added and the mixture was stirred for 30 minutes. It was cooled to room temperature and poured onto 500 g of ice. The solid which formed was separated by filtration, washed well with water and allowed to dry on a porous plate to give a dark-orange solid. This solid was slurried in 210 ml of warm aqeuous methanol to give, after filtration and drying, N-(1H-tetrazol-5-yl)-N'-(4-ethyl-5-methyl-3-carbethoxythiophen-2-yl)formamidine as off-white crystals. A slurry of 6 g of the crude formamidine in 75 ml of methanol was stirred at room temperature as 4 ml of 5 N aqueous sodium hydroxide solution was added dropwise. The homogeneous solution was heated at 70° C. for 6.5 hours and then cooled to room temperature. The solvent was evaporated in vacuo and the residue was taken up in hot aqueous 2-propanol for recrystallization. The crude solid obtained was recrystallized again from hot aqueous 2propanol to give 3-(1H-tetrazol-5-yl)-5-ethyl-6-methylthieno[2,3-d]pyrimidin-4(3H)-one, sodium salt monohydrate, melting at greater than 300° C.

EXAMPLE 9

To a mixture of 9.4 ml of triethoxymethane, 4.8 g of 5-aminotetrazole and 25 ml of dimethylformamide was heated at 100° C. for 2 hours. A solution of 12 g of ethyl 2-amino-4,5-trimethylenethiophene-3-carboxylate in 15 ml of dimethylformamide was then added. The mixture was stirred for 5 minutes and then cooled to room temperature. The solid which formed was collected by filtration, washed first with dimethylformamide and then with tetrachloromethane and dried in a vacuum oven to give 10.9 g of an approximately 1:1 mixture of N-(1H-tetrazol-5-yl)-N'-(3-carbethoxy-4,5trimethylenethiophen-2-yl)formamidine and bis-N,N'-(2-carbethoxy-4,5-trimethylenethiophen-2-yl)formamidine. The product thus obtained was combined with an additional 4.1 g of the same crude formamidine which was obtained in a similar way. The resulting mixture was triturated twice with 110 ml of hot tetrachloromethane/methanol (10:1). The solid was filtered, washed with methanol and dried in a vacuum oven to give 7.9 g of crude formamidine. A slurry of 7.75 g of this crude formamidine in 45 ml of methanol was stirred at room temperature while 5.1 ml of 5 N aqueous sodium hydroxide was added dropwise. The mixture was then heated at reflux for 24 hours and cooled to room temperature. The solid which formed was separated by filtration and dried in a vacuum oven to give crude 3-(1H-tetrazol-5-yl)-5,6-trimethylenethieno[2,3-d]pyrimidin-4(3e,uns/H/ )-one, sodium salt. Recrystallization of this crude material from hot aqueous 2-propanol gave purified product as a monohydrate melting at greater than 300° C.

EXAMPLE 10

A slurry of 6.1 g of N-(1H-tetrazol-5-yl)-N'-(5-methyl-3-carbethoxythiophen-2-yl)formamidine in 40 ml methanol was stirred at room temperature and 4.4 ml of 5 N aqueous sodium hydroxide was added dropwise. The mixture initially became homogeneous but, after 15 minutes, a solid precipitated. The mixture was stirred for a further 30 minutes and then the solid was separated by filtration, washed with tetrachloromethane and briefly with cold methanol, and dried in a vacuum oven to give 3-(1H-tetrazol-5-yl)-6-methylthieno[2,3-d]pyrimidin-4(3H)-one, sodium salt, melting at greater than 300° C.

EXAMPLE 11

A slurry of 10 g of N-(1H-tetrazol-5-yl)-N'-(2-carbethoxy-4,5-dimethylthiophen-2-yl)formamid and 30 ml of water was stirred at room temperature while 6.5 ml of 5 N aqueous sodium hydroxide solution was slowly added dropwise. The mixture became almost homogeneous before a new solid formed. It was then heated to reflux and became homogeneous before it was cooled again to room temperature. The crystals which formed were separated by filtration, washed with 2-propanol and then tetrachloromethane and dried in a vacuum oven to give 3-(1H-tetrazol-5-yl)-5,6-dimethylthieno[2,3-d]pyrimidin-4(3H)-one, sodium salt, 0.75 hydrate, melting at greater than 280° C. Acidification of an aqueous solution of this product gives 3(1H-tetrazol-5-yl)-5,6-dimethylthieno[2,3-d]pyrimidin-4(3H)-one. This compound has the following structural formula:

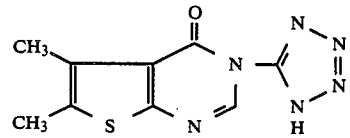

EXAMPLE 12

A slurry of 6 g of N-(1Htetrazol-5-yl)-N'-(2-carbethoxy-4,5-tetramethylenethiophen-2-yl)formamidine in 60 ml of 2-propanol and 9 ml of water was stirred at room temperature while 2.4 ml of 7.9 N aqueous sodium hydroxide was added dropwise. The mixture was stirred at room temperature for 1 hour and then heated at reflux for 2 hours before being cooled to room temperature. The solid which formed was separated by filtration, washed with 2-propanol and dried in a vacuum oven to give 3-(1H-tetrazol-5-yl)5,6-tetramethylenethieno[2,3-d]pyrimidin-4(3H)-one, sodium salt dihydrate, melting at greater than 300° C. Acidification of an aqueous solution of this product gives 3-(1Htetrazol-5-yl)-5,6-tetramethylenethieno[2,3-d]pyrimidin4(3H)-one. This compound has the following structural formula:

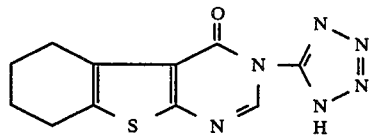

EXAMPLE 13

If the procedure of Example 3 is repeated using ethyl 2-aminothiophene-3-carboxylate in place of the ethyl 2-amino-5-methylthiophene-3-carboxylate, the product obtained is N-(1H-tetrazol-5-yl)-N'-(3-carbethoxythiophen-2-yl)formamidine. When this formamidine is reacted with aqueous sodium hydroxide according to the procedure described in Example 10, the product obtained is 3-(1H-tetrazol-5-yl)thieno[2,3-d]pyrimidin-4(3H)-one, sodium salt.

EXAMPLE 14

If the procedure of Example 6 is repeated using triethoxyethane and acetic acid in place of the triethoxymethane and formic acid, there is first obtained N-(1-Htetrazol-5-yl)-N'-(5-propyl-3-carbethoxythiophen-2-yl)acetamidine. When this acetamidine is treated with base as described in Example 6, there is then obtained 3-(1Htetrazol-5-yl)-2-methyl-6-propylthieno[2,3-d]pyrimidin-4(3H)- one, sodium salt.

3-(1H-Tetrazol-5-yl)-2-ethyl-6-propylthieno[2,3-d]pyrimidin-4(3H)-one, sodium salt, is obtained in a similar way using the appropriate starting materials.

What is claimed is:

1. A compound of the formula

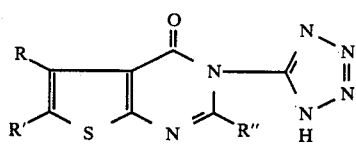

wherein R is hydrogen or lower alkyl having 1 to 4 carbon atoms; R' is hydrogen, lower alkyl having 1 to 4 carbon atoms or phenyl; or R and R' are combined as trimethylene or tetramethylene; and R" is hydrogen, methyl or ethyl; and the pharmaceutically acceptable salts thereof.

2. A compound according to claim 1 which has the formula

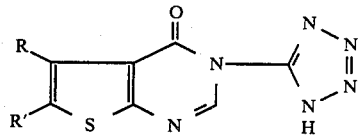

wherein R is hydrogen or lower alkyl having 1 to 4 carbon atoms; R' is hydrogen, lower alkyl having 1 to 4 carbon atoms or phenyl; or R and R' are combined as trimethylene or tetramethylene; and the alkali metal salts thereof.

3. A compound according to claim 1 which is 3-(1Htetrazol-5-yl)-6-propylthieno[2,3-d]pyrimidin-4(3H)-one.

4. A compound according to claim 1 which is 3-(1Htetrazol-5-yl)-5,6-dimethylthieno[2,3-d]pyrimidin-4(3H)-tetrazol-5-yl)-5,6-tetramethylenethieno[2,3-d]pyromidin-one.

5. A compound according to claim 1 which is 3-(1H4(3H)-one.

* * * * *

UNITED STATES PATENT AND TRADEMARK OFFICE
CERTIFICATE OF CORRECTION

PATENT NO. : 4,761,474
DATED : August 2, 1988
INVENTOR(S) : Norton P. Peet, Shyam Sunder, Anna P. Vinogradoff It is certified that error appears in the above-identified patent and that said Letters Patent is hereby corrected as shown below:

Column 4, Line 28, patent reads: "control animals" and should read --control animals.--.
Column 5, Line 22, patent reads: "5aminotetrazole," and should read --5-aminotetrazole,--.
Column 7, Line 8, patent reads: "2propanol" and should read --2-propanol--.
Column 7, Line 24, patent reads: "(3-carbethoxy-4,5trimethy-" and should read --(3-carbethoxy-4,5-trimethy---.
Column 7, Line 40, patent reads: "pyrimidin-4(3e,uns/H/ )-one," and should read --pyrimidin-4(3H)-one,--.
Column 7, Line 61, patent reads: "formamid and 30ml of water" and should read --formamidine in 60 ml of 2-propanol and 30 ml of water--.
Column 8, Line 18, patent reads: "N-(1Htetrazol" and should read --N-(1H-tetrazol--.
Column 8, Line 31, patent reads: "3-(1Htetrazol-" and should read --3-(1H-tetrazol--.
Column 8, line 32, patent reads: "d]pyrimidin4" and should read --d]pyrimidin-4--.
Column 8, Line 58, patent reads: "(1-Htetrazol" and should read --(1H-tetrazol--.
Column 8, Line 62, patent reads: "(1Htetrazol" and should read --(1H-tetrazol--.
Column 10, Line 14, patent reads: "(1Htetrazol" and should read --(1H-tetrazol--.
Column 10, Line 18, patent reads: "(1Htetrazol" and should read --(1H-tetrazol--.
Column 10, Line 19, patent reads: "4(3H)-tetrazol-5-yl)-5,6-tetramethylenethieno[2,3-d]pyromidin-one." and should read -- -4(3H)-one.--.
Column 10, Line 21 patent reads: "3-(1H4(3H)-one" and should read -- 3-(1H-tetrazol-5-yl)-5,6-tetramethylenethieno[2,3-d]pyrimidin-4(3H)-one.--

Signed and Sealed this

Twenty-first Day of April, 1992

Attest:

HARRY F. MANBECK, JR.

*Attesting Officer*  *Commissioner of Patents and Trademarks*